United States Patent
Bell et al.

(10) Patent No.: US 7,032,751 B2
(45) Date of Patent: Apr. 25, 2006

(54) DISPENSING ASSEMBLY FOR SINGLE PIECE FACE MASK

(75) Inventors: Daryl Steven Bell, Appleton, WI (US); Naveen Agarwal, Atlanta, GA (US); Michael Andrew Amante, Arlington, VA (US); Jeffrey M. Willis, Atlanta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 438 days.

(21) Appl. No.: 10/325,247

(22) Filed: Dec. 19, 2002

(65) Prior Publication Data

US 2004/0121107 A1 Jun. 24, 2004

(51) Int. Cl.
| | |
|---|---|
| B65D 85/67 | (2006.01) |
| A42B 1/18 | (2006.01) |
| A62B 18/02 | (2006.01) |
| B65H 1/00 | (2006.01) |

(52) U.S. Cl. ............. 206/390; 2/9; 2/206; 128/206.19; 128/863; 206/820; 221/45

(58) Field of Classification Search ................ 206/390, 206/438–440, 820; 2/9, 424, 206; 128/206.12–29, 128/207.11–13, 863, 206.19, 206.21; 221/33, 221/45

See application file for complete search history.

(56) References Cited

U.S. PATENT DOCUMENTS

| | | | |
|---|---|---|---|
| 2,142,282 A | 1/1939 | Norton | |
| 2,634,725 A | 4/1953 | Presti | |
| 3,131,399 A * | 5/1964 | Murphy et al. | ............. 206/390 |
| 3,338,992 A | 8/1967 | Kinney | |
| 3,341,394 A | 9/1967 | Kinney | |
| 3,502,763 A | 3/1970 | Hartmann | |
| 3,542,615 A | 11/1970 | Dobo et al. | |
| D224,277 S | 7/1972 | Venaleck | |
| 3,692,618 A | 9/1972 | Dorschner et al. | |
| 3,735,865 A * | 5/1973 | Smith | .......................... 206/390 |
| 3,802,817 A | 4/1974 | Matsuki et al. | |
| 3,849,241 A | 11/1974 | Butin et al | |
| 3,851,760 A * | 12/1974 | Smith | .......................... 206/390 |
| 3,886,597 A | 6/1975 | Dupre | |
| 3,953,566 A | 4/1976 | Gore | |
| 4,014,047 A | 3/1977 | Zobel | |
| 4,084,585 A | 4/1978 | Venaleck | |

(Continued)

FOREIGN PATENT DOCUMENTS

GB 2299762 A 10/1996

*Primary Examiner*—Bryon P. Gehman
(74) *Attorney, Agent, or Firm*—Dority & Manning (57) ABSTRACT

A method of producing a plurality of face masks is provided. The method includes the step of providing a continuous web that is of the same material throughout. A plurality of body portions are stamped from the continuous web so that each of the plurality of face masks has one body portion. A plurality of left extension portions are stamped from the continuous web so that each of the body portions has one left extension portion integrally attached thereto. A plurality of right extension portions are stamped from the continuous web so that each of the body portions has one right extension portion integrally attached thereto. A dispenser assembly for dispensing face masks is also provided. The assembly includes a core and a roll of face masks that are rotatably disposed on the core. As least one of the face masks includes a body portion and left extension portion that is integrally attached to the body portion. A right extension portion is integrally attached to the body portion.

18 Claims, 8 Drawing Sheets

U.S. PATENT DOCUMENTS

| | | |
|---|---|---|
| 4,100,324 A | 7/1978 | Anderson et al. |
| 4,187,390 A | 2/1980 | Gore |
| 4,195,629 A | 4/1980 | Halford |
| 4,215,682 A | 8/1980 | Kubik et al. |
| 4,300,240 A | 11/1981 | Edwards |
| 4,340,563 A | 7/1982 | Appel et al. |
| 4,374,888 A | 2/1983 | Bornslaeger |
| 4,375,718 A | 3/1983 | Wadsworth et al. |
| 4,443,513 A | 4/1984 | Meitner et al. |
| 4,520,509 A | 6/1985 | Ward |
| 4,550,856 A | 11/1985 | Ballmann et al. |
| 4,592,815 A | 6/1986 | Nakao |
| 4,630,310 A * | 12/1986 | Winesett ................ 206/820 |
| 4,631,933 A | 12/1986 | Carey, Jr. |
| 4,641,379 A | 2/1987 | Martin |
| 4,652,487 A | 3/1987 | Morman |
| 4,655,760 A | 4/1987 | Morman et al. |
| 4,657,802 A | 4/1987 | Morman |
| 4,720,415 A | 1/1988 | Vander Wielen et al. |
| 4,781,966 A | 11/1988 | Taylor |
| 4,789,699 A | 12/1988 | Kieffer et al. |
| 4,790,307 A | 12/1988 | Haber et al. |
| 4,802,473 A | 2/1989 | Hubbard et al. |
| 4,818,464 A | 4/1989 | Lau |
| 4,825,474 A | 5/1989 | Edwards |
| 4,874,659 A | 10/1989 | Ando et al. |
| 4,891,957 A | 1/1990 | Strack et al. |
| 4,965,122 A | 10/1990 | Morman |
| 4,969,457 A | 11/1990 | Hubbard et al. |
| 4,981,747 A | 1/1991 | Morman |
| 5,020,533 A | 6/1991 | Hubbard et al. |
| 5,035,006 A | 7/1991 | Hetz et al. |
| 5,107,547 A | 4/1992 | Scheu |
| 5,114,781 A | 5/1992 | Morman |
| 5,214,804 A | 6/1993 | Carey et al. |
| 5,226,992 A | 7/1993 | Morman |
| 5,240,755 A * | 8/1993 | Zimmer ................ 206/820 |
| 5,244,482 A | 9/1993 | Hassenboehler, Jr. et al. |
| 5,265,280 A | 11/1993 | Walsh |
| 5,322,061 A | 6/1994 | Brunson |
| 5,336,545 A | 8/1994 | Morman |
| 5,383,450 A | 1/1995 | Hubbard et al. |
| 5,401,446 A | 3/1995 | Tsai et al. |
| 5,401,466 A | 3/1995 | Foltz et al. |
| 5,425,380 A | 6/1995 | Hudson et al. |
| 5,492,753 A | 2/1996 | Levy et al. |
| 5,493,753 A | 2/1996 | Rostamo |
| 5,540,976 A | 7/1996 | Shawver et al. |
| 5,553,608 A | 9/1996 | Reese et al. |
| 5,628,308 A | 5/1997 | Harges et al. |
| 5,681,645 A | 10/1997 | Strack et al. |
| 5,693,401 A | 12/1997 | Sommers et al. |
| 5,699,791 A | 12/1997 | Sukiennik et al. |
| 5,704,349 A * | 1/1998 | Hubbard et al. ....... 128/206.19 |
| 5,706,803 A * | 1/1998 | Bayer ................ 128/206.19 |
| 5,717,991 A | 2/1998 | Nozaki et al. |
| 5,735,270 A * | 4/1998 | Bayer ................ 128/206.19 |
| 5,813,398 A | 9/1998 | Baird et al. |
| 5,817,584 A | 10/1998 | Singer et al. |
| 5,819,935 A | 10/1998 | Lawson |
| 5,845,340 A | 12/1998 | Frislie |
| 5,863,312 A | 1/1999 | Wolfe |
| 5,934,275 A | 8/1999 | Gazzara |
| 6,119,691 A | 9/2000 | Angadjivand et al. |
| 6,148,817 A | 11/2000 | Bryant et al. |
| 6,162,535 A | 12/2000 | Turkevich et al. |
| 6,338,340 B1 | 1/2002 | Finch et al. |
| 6,474,336 B1 | 11/2002 | Wolfe |
| 6,524,294 B1 | 2/2003 | Hilston et al. |
| 6,543,450 B1 | 4/2003 | Flynn |
| 6,574,801 B1 * | 6/2003 | Harens et al. ................ 2/206 |
| 6,615,838 B1 | 9/2003 | Tsai |
| 6,632,212 B1 | 10/2003 | Morman et al. |
| 6,644,314 B1 * | 11/2003 | Elsberg ................ 128/206.21 |
| 6,656,403 B1 | 12/2003 | Clune et al. |
| 2002/0162556 A1 | 11/2002 | Smith |
| 2003/0045856 A1 | 3/2003 | Jaafar |

\* cited by examiner

FIG.14b

DISPENSING ASSEMBLY FOR SINGLE PIECE FACE MASK

BACKGROUND

Face masks find utility in a variety of manufacturing, custodial, and household applications. In these types of applications, face masks filter out dust and other contaminates to facilitate easier breathing on the part of the user. Likewise, face masks have found utility in the healthcare industry. In this regard, face masks are helpful in that they may be configured to filter exhaled air from the wearer to minimize the amount of bacteria or other contaminants released from the user into the environment. Such a limitation of bacteria contaminants is important in that typically hospital patients require a sterile environment in order to avoid infections, and hospital patients often have compromised immune systems making them susceptible to infection. Additionally, face masks may also filter inhaled air to protect the user from contaminants that may be found in a hospital setting, as hospital patients commonly carry airborne bacterial pathogens.

It is therefore the case that in the health care field, specifically in operating rooms, health care providers often use face masks to protect themselves from acquiring harmful diseases such as AIDS and hepatitis along with other contagious diseases that may be present in the patients that are being treated.

Face masks have also been designed in order to provide a tight sealing arrangement. Such a sealing arrangement may prove useful in preventing the transfer of pathogens that reside in bodily fluids or other liquids. As such, face masks have been designed in order to prevent airborne pathogens and/or pathogens in fluids from being transferred to and/or from the health care provider.

Some face masks are configured to cover the entire face of a user while other face masks are designed to cover only the nose and mouth of the user. Additionally, face masks have been designed to cover various parts of a user's face. For instance, certain face masks are configured for covering the nose, eyes, and mouth of a user. The section of the face mask that covers the nose and mouth typically is composed of a material that prevents the passage of germs and other contaminants therethrough but allows for the passage of air so that the user may breathe. This section is typically known as a front panel or body portion. Attached to this front panel is a securing device that is used for attaching the front panel securely to the head of the user. For instance, manual tie straps are often employed. For this purpose the front panel of the face mask is placed on the face of the user and the tie straps are extended around the head of the user and tied. The straps fasten the face mask to the user.

In order to construct a face mask that has tie straps and a front panel, the two parts are created separately and then attached to one another. For instance, the tie straps are typically attached to the front panel by means of staples, adhesive, or various types of mechanical fastenings. As such, several different parts go into the construction of face masks. It is therefore the case that components of the face mask are formed in separate processes and are then assembled onto one another in additional processes. Performing these extra manufacturing steps adds to the cost of the final product and also adds to the time it takes to construct the face mask.

Additionally, face masks that are constructed from various parts that are attached to one another have also been known to break at these attachment points. For instance, an elastic band may be employed on the face mask in order to retain the front panel onto the head or face of the user. Face masks of this type have been known to break at the attachment point between the front panel and the elastic band. Face masks being composed of several different parts are therefore less structurally sound than would be a face mask that is composed of a single piece. Also, apertures that may be present at the connection points between the front panel of the face mask and the manual tie straps or elastic band, that is employed to retain the front panel on the face or head of the user, may have apertures present that allow for the transfer of pathogens to or from the wearer of the face mask.

Also, prior face masks have been sometimes composed of several layers of different material that are used to provide a sealing arrangement to the face of the wearer and to filter pathogens. These complex arrangements are disadvantageous because they employ different types of materials and require several manufacturing steps in order to construct the final product.

Face masks are sometimes provided in a dispenser from which an individual face mask may be obtained by a wearer. Items dispensed from a dispenser are typically low in cost and are disposable. Therefore, it is usually important to be able to dispense these items inexpensively without damage to the product.

Prior dispensers for face masks have typically included a container into which a nested stack of face masks were placed. The face mask to be dispensed from the container was typically positioned at an exterior opening of the carton and an elastic band or tie strap that was attached to this face mask was hung out of the carton. A user would dispense this face mask by grasping the elastic band or tie strap and pulling down, thereby causing the face mask onto which it is attached to be removed from the carton. Subsequently, a new face mask to be dispensed would fall into the place of the previously dispensed face mask, and the elastic band or tie straps of the next to be dispensed face mask would protrude from the carton. These types of dispensing arrangements suffer from the disadvantage of commonly dispensing more than one face mask when a user pulls on the elastic band or tie straps. Also, such an arrangement may also fail to have the next to be dispensed face mask being positioned in the dispensing position upon the removal of a preceding face mask. In this instance, the user must reach into the carton in order to grasp the face mask to be removed. This could cause the face mask to be damaged upon being grasped and pulled by the user.

The present invention provides for a single piece face mask that alleviates problems encountered in the design and/or dispensing found in prior face mask designs and dispensing arrangements.

SUMMARY

Various features and advantages of the invention will be set forth in part in the following description, or may be obvious from the description, or may be learned from practice of the invention.

The present invention includes a face mask that has a body portion that is configured to be placed over a mouth and at least part of a nose of a user. The body portion contacts at least a portion of the skin of the user's face. A first extension portion is present and is integrally attached to the body portion. The first extension portion is configured to at least partially extend around at least a portion of the head of the user. The first extension portion is made of the same material as the body portion. A second extension portion is integrally attached to the body portion. The second extension portion is also made of the same material as the body portion. A hook and loop type fastener is present. One of the hook and loop sections is carried by the first extension portion, and the other of the hook and loop sections is carried by the second extension portion. Engagement of the hook section and the loop section causes the body portion, the first extension portion, and the second extension portion to be retained on the user. Disengagement of the hook section and the loop section causes the body portion, the first extension portion, and the second extension portion to be released from the user.

The face mask may also be configured so that the second extension portion extends around at least a portion of the user's head. Also, the first and second extension portions may be retained on the user's ears by an aperture in the first extension portion and an aperture in the second extension portion.

In certain exemplary embodiments of the present invention, the hook section may be integrally formed with one of the first or second extension portions, and the hook section may be integrally formed with the other of the first or second extension portions.

A further exemplary embodiment of the present invention exists in a face mask as described above where the body portion has a formed cavity on the surface of the body portion to provide a better fit for the user's mouth. Also, the body portion may be single layered or multi-layered in other exemplary embodiments of the present invention. Additionally, a wire or any rigid material may be carried by the body portion and create a section of structural rigidity on the body portion in order to further shape the face mask to better conform and/or seal on the face of the user.

In other exemplary embodiments of the present invention, the face mask may be made of an elastic meltblown nonwoven web, and in some instances the web is an electret. Also, in other exemplary embodiments, the body portion, the left extension portion, and the right extension portion may be extensible and retractable in one or more directions.

Also included in the present invention is a method of producing face masks which includes the step of providing a continuous web of material. A plurality of face masks are die cut from the continuous web of material. The face masks include a body portion, a left extension portion that is integrally attached to the body portion, and a right extension portion that is also integrally attached to the body portion.

A further step may be added in which an aperture is die cut into the left extension portion and die cut into the right extension portion. Alternatively, a right punch out member may be die cut into the right extension portion instead of placing an aperture into the right extension portion. Also, a left punch out member may be die cut into the left extension portion as opposed to placing an aperture in the left extension portion.

Also included in the present invention is a method of producing face masks as described above where the continuous web of material includes a plurality of layers. Additionally, the invention provides for a method where the plurality of layers are made of different materials.

An additional method of producing a plurality of face masks is also provided. Here, a continuous web that is of the same material throughout is used. A plurality of body portions are stamped into the continuous web so that each of the plurality of face masks has one body portion. Additionally, a plurality of left extension portions are stamped into the continuous web so that each of the body portions of the plurality of face masks has one left extension portion being integrally attached thereto. Also, a plurality of right extension portions are stamped into the continuous web so that each of the body portions has one right extension portion being integrally attached thereto.

Also included in the present invention is a dispenser assembly for dispensing face masks. The dispenser assembly includes a core and a roll of face masks that are rotatably disposed on the core. The face mask includes a body portion, a left extension portion that is integrally attached to the body portion, and a right extension portion that is integrally attached to the body portion.

The dispenser assembly of the present invention may be constructed wherein the roll of face masks is a continuous web of material that has the face masks disposed thereon. Additionally, the core of the dispenser assembly may be a cylindrical core in certain exemplary embodiments. Also, the roll of face masks may be dispensed from the core by pulling a leading face mask from the roll and disengaging the leading face mask from a trailing face mask. Also, when a continuous web of material is used, the face masks may be dispensed from the core by disengaging one of the face mask from the continuous web of material.

The dispenser assembly may also be arranged so that the roll of face masks have one of the left extension portions of one of the face masks proximate to one of the right extension portions of another of the face masks. A perforation exists between the right and left extension portions. The face masks may be disengaged from one another by tearing this perforation between the face masks.

DEFINITIONS

As used herein, the term "nonwoven fabric or web" means a web having a structure of individual fibers or threads which are interlaid, but not in an identifiable manner as in a knitted fabric. Nonwoven fabrics or webs have been formed from various processes such as, for example, meltblowing processes, spunbonding processes, and bonded carded web processes. The basis weight of nonwoven fabrics is usually expressed in ounces of material per square yard (osy) or grams per square meter (gsm) and the fiber diameters are usually expressed in microns. (Note that to convert from osy to gsm, multiply osy by 33.91).

As used herein, the term "spunbonded fibers" refers to small diameter fibers which are formed by extruding molten thermoplastic material as filaments from a plurality of fine, usually circular capillaries of a spinneret with the diameter of the extruded filaments then being rapidly reduced to fibers as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartman, and U.S. Pat. No. 3,542,615 to Dobo et al., the contents of which are incorporated herein by reference in their entirety. Spunbond fibers are generally continuous and have diameters generally greater than about 7 microns, more particularly, between about 10 and about 20 microns. As used herein, the term "meltblown fibers" means fibers formed by extruding a molten thermoplastic material through a plurality of fine, usually circular, die capillaries as molten threads or filaments into converging high velocity, usually hot, gas (e.g. air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241 to Butin et al., the content of which is incorporated herein by reference in its entirety. Meltblown fibers are microfibers which may be continuous or discontinuous with diameters generally less than 10 microns.

As used herein, the term "composite" refers to a material which may be a multicomponent material or a multilayer material. These materials may include, for example, stretch bonded laminates, neck bonded laminates, or any combination thereof.

As used herein, the term "stretch bonded laminate" refers to a composite material having at least two layers in which one layer is a gatherable layer and the other layer is an elastic layer. The layers are joined together when the elastic layer is extended from its original condition so that upon relaxing the layers, the gatherable layer is gathered. Such a multilayer composite elastic material may be stretched to the extent that the nonelastic material gathered between the bond locations allows the elastic material to elongate. One type of stretch bonded laminate is disclosed, for example, by U.S. Pat. No. 4,720,415 to Vander Wielen et al., the content of which is incorporated herein by reference in its entirety. Other composite elastic materials are disclosed in U.S. Pat. No. 4,789,699 to Kieffer et al., U.S. Pat. No. 4,781,966 to Taylor and U.S. Pat. Nos. 4,657,802 and 4,652,487 to Morman and 4,655,760 to Morman et al., the contents of which are incorporated herein by reference in their entirety.

As used herein, the terms "necking" or "neck stretching" interchangeably refer to a method of elongating a nonwoven fabric, generally in the machine direction, to reduce its width (cross-machine direction) in a controlled manner to a desired amount. The controlled stretching may take place under cool, room temperature or greater temperatures and is limited to an increase in overall dimension in the direction being stretched up to the elongation required to break the fabric, which in most cases is about 1.2 to 1.6 times. When relaxed, the web retracts toward, but does not return to, its original dimensions. Such a process is disclosed, for example, in U.S. Pat. No. 4,443,513 to Meitner and Notheis, U.S. Pat. Nos. 4,965,122, 4,981,747 and 5,114,781 to Morman and U.S. Pat. No. 5,244,482 to Hassenboehier Jr. et al., the contents of which are incorporated herein by reference in their entirety.

As used herein, the term "necked material" refers to any material which has undergone a necking or neck stretching process.

As used herein, the term "reversibly necked material" refers to a material that possesses stretch and recovery characteristics formed by necking a material, then heating the necked material, and cooling the material. Such a process is disclosed in U.S. Pat. No. 4,965,122 to Morman, commonly assigned to the assignee of the present invention, and incorporated by reference herein in its entirety. As used herein, the term "neck bonded laminate" refers to a composite material having at least two layers in which one layer is a necked, non-elastic layer and the other layer is an elastic layer. The layers are joined together when the non-elastic layer is in an extended (necked) condition. Examples of neck-bonded laminates are such as those described in U.S. Pat. Nos. 5,226,992, 4,981,747, 4,965,122 and 5,336,545 to Morman, the contents of which are incorporated herein by reference in their entirety.

As used herein, the term "coform" means a meltblown material to which at least one other material is added during the meltblown material formation. The meltblown material may be made of various polymers, including elastomeric polymers. Various additional materials may be added to the meltblown fibers during formation, including, for example, pulp, superabsorbent particles, cellulose or staple fibers. Coform processes are illustrated in commonly assigned U.S. Pat. No. 4,818,464 to Lau and U.S. Pat. No. 4,100,324 to Anderson et al., the contents of which are incorporated herein by reference in their entirety.

As used herein, the term "stitchbonded" refers to a process in which materials (fibers, webs, films, etc.) are joined by stitches sewn or knitted through the materials. Examples of such processes are illustrated in U.S. Pat. No. 4,891,957 to Strack et al. and U.S. Pat. No. 4,631,933 to Carey, Jr., the contents of which are incorporated herein by reference in their entirety.

As used herein, the term "ultrasonic bonding" refers to a process in which materials (fibers, webs, films, etc.) are joined by passing the materials between a sonic horn and anvil roll. An example of such a process is illustrated in U.S. Pat. No. No. 4,374,888 to Bornslaeger, the content of which is incorporated herein by reference in its entirety.

As used herein, the term "thermal point bonding" involves passing materials (fibers, webs, films, etc.) to be bonded between a heated calender roll and an anvil roll. The calender roll is usually, though not always, patterned in some way so that the entire fabric is not bonded across its entire surface, and the anvil roll is usually flat. As a result, various patterns for calender rolls have been developed for functional as well as aesthetic reasons. Typically, the percent bonding area varies from around 10 percent to around 30 percent of the area of the fabric laminate. As is well known in the art, thermal point bonding holds the laminate layers together and imparts integrity to each individual layer by bonding filaments and/or fibers within each layer.

As used herein, the term "elastic" refers to any material, including a film, fiber, nonwoven web, or combination thereof, which upon application of a biasing force, is stretchable to a stretched, biased length which is at least about 150 percent, or one and a half times, its relaxed, unstretched length, and which will recover at least 15 percent of its elongation upon release of the stretching, biasing force.

As used herein, the term "extensible and retractable" refers to the ability of a material to extend upon stretch and retract upon release. Extensible and retractable materials are those which, upon application of a biasing force, are stretchable to a stretched, biased length and which will recover a portion, preferably at least about 15 percent, of their elongation upon release of the stretching, biasing force.

As used herein, the terms "elastomer" or "elastomeric" refer to polymeric materials that have properties of stretchability and recovery.

As used herein, the term "stretch" refers to the ability of a material to extend upon application of a biasing force. Percent stretch is the difference between the initial dimension of a material and that same dimension after the material has been stretched or extended following the application of a biasing force. Percent stretch may be expressed as [(stretched length—initial sample length)/initial sample length]×100. For example, if a material having an initial length of one (1) inch is stretched 0.50 inch, that is, to an extended length of 1.50 inches, the material can be said to have a stretch of 50 percent.

As used herein, the term "recover" or "recovery" refers to a contraction of a stretched material upon termination of a biasing force following stretching of the material by application of the biasing force. For example, if a material having a relaxed, unbiased length of one (1) inch is elongated 50 percent by stretching to a length of one and one half (1.5) inches the material would have a stretched length that is 150 percent of its relaxed length. If this exemplary stretched material contracted, that is recovered to a length of one and one tenth (1.1) inches after release of the biasing and stretching force, the material would have recovered 80 percent (0.4 inch) of its elongation.

As used herein, the term "electret" or "electret treating" refers to a treatment that imparts a charge to a dielectric material, such as a polyolefin. The charge includes layers of positive or negative charges trapped at or near the surface of the polymer, or charge clouds stored in the bulk of the polymer. The charge also includes polarization charges which are frozen in alignment of the dipoles of the molecules. Methods of subjecting a material to electret treating are well known by those skilled in the art. These methods include, for example, thermal, liquid-contact, electron beam, and corona discharge methods. One particular technique of subjecting a material to electret treating is disclosed in U.S. Pat. No. 5,401,466, the contents of which is herein incorporated in its entirety by reference. This technique involves subjecting a material to a pair of electrical fields wherein the electrical fields have opposite polarities.

As used herein, the term "polymer" generally includes but is not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configurations of the molecule. These configurations include, but are not limited to isotactic, syndiotactic and random symmetries.

As used herein, any given range is intended to include any and all lesser included ranges. For example, a range of from 45–90 would also include 50–90; 45–80; 46–89; and the like.

BRIEF DESCRIPTION OF THE DRAWINGS

FIG. 7 is a perspective view of an exemplary embodiment of a face mask in accordance with the present invention. The face mask is shown as being worn by a user and including at least one heat seal, a nose wire, a chin wire and at least two body portion wires.

DETAILED DESCRIPTION

Reference will now be made in detail to embodiments of the invention, one or more examples of which are illustrated in the drawings. Each example is provided by way of explanation of the invention, and not meant as a limitation of the invention. For example, features illustrated or described as part of one embodiment can be used with another embodiment to yield still a third embodiment. It is intended that the present invention include these and other modifications and variations.

Figure 1:
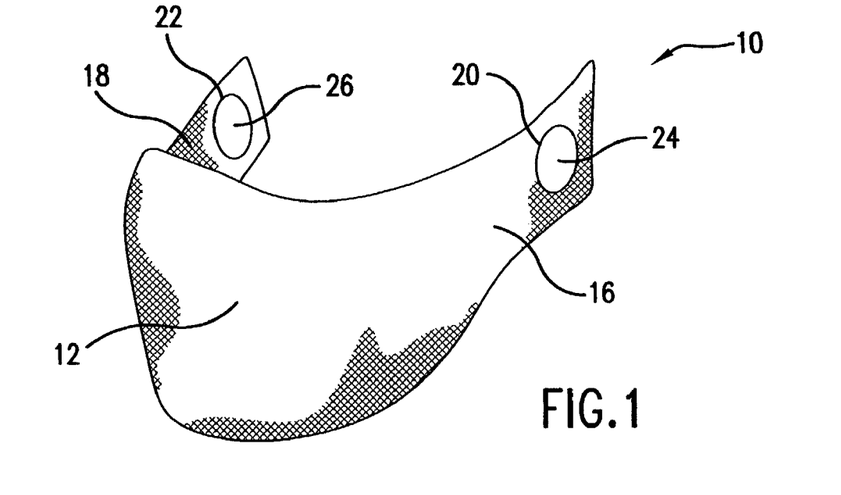
FIG. 1 is a perspective view of an exemplary embodiment of a face mask in accordance with the present invention.

A face mask 10 in accordance with the present invention is shown in FIG. 1. The face mask 10 includes a body portion 12 from which a first extension portion 16 and second extension portion 18 extend therefrom. The first extension portion 16 and second extension portion 18 are integrally formed with the body portion 12. These three parts of the face mask 10 are formed of the same material. It is therefore the case that the first and second extension portions 16 and 18 are not independent, discontinuous structures, but are instead integrated into a single unit. The face mask 10 shown in FIG. 1 is a single layer of material.

The body portion 12 may be configured to be placed over the mouth and at least part of the nose of the user 14. In order to at least partially isolate these two parts of the user 14 from the environment. The body portion 12 may contact at least a portion of the skin of the user's face. In one exemplary embodiment of the present invention, the first extension portion 16 may be a left extension portion that is configured to extend around the left side of the user's 14 head. Additionally, the second extension portion 18 may be a right extension portion 18 that extends around the right side of the user's 14 head.

The first extension portion 16 includes a left ear attachment member 20. In this case, the left ear attachment member 20 is an aperture 24. Likewise, the second extension portion 18 includes a right ear attachment member 22. Again, the right ear attachment member 22 in this exemplary embodiment of the present invention is an aperture 26.

Figure 2:
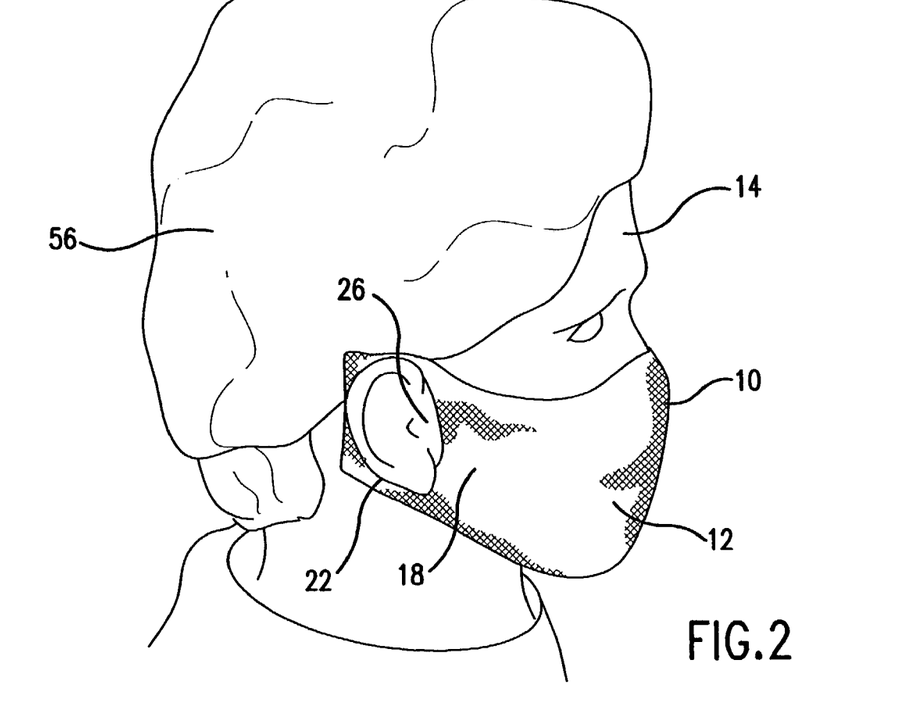
FIG. 2 is a perspective view of the exemplary embodiment of the face mask shown in FIG. 1 being worn by a user.

The face mask 10 of FIG. 1 is shown as being worn by a user 14 in FIG. 2. Here, the face mask 10 is placed around the face of the user 14 so that the body portion 12 of the face mask 10 covers the mouth and nose of the user 14. Additionally, the body portion 12 contacts the face of the user 14 and provides a seal so that contaminants may only pass to and from the nose and mouth of the user 14 via the body portion 12. The face mask 10 is attached to the face of the user 14 by the right ear attachment member 22 and the left ear attachment member 20. Here, the right ear attachment member 22 includes an aperture 26 through which the right ear of the user 14 is placed. Although, not shown in FIG. 2., the aperture 24 included in the left ear attachment member 20 has the left ear of the user 14 extending therethrough. In this manner, the face mask 10 may be retained on the face of the user 14 during use.

By providing the face mask 10 of a single material, the left ear attachment 20 and the right ear attachment member 22 may have the apertures 24 and 26 cut from the material composing the face mask 10. The face mask 10 of the present invention may therefore utilize a single piece of material in which the first and second extension portions 16 and 18 along with the body portion 12 form a unity integral structure.

Figure 3:
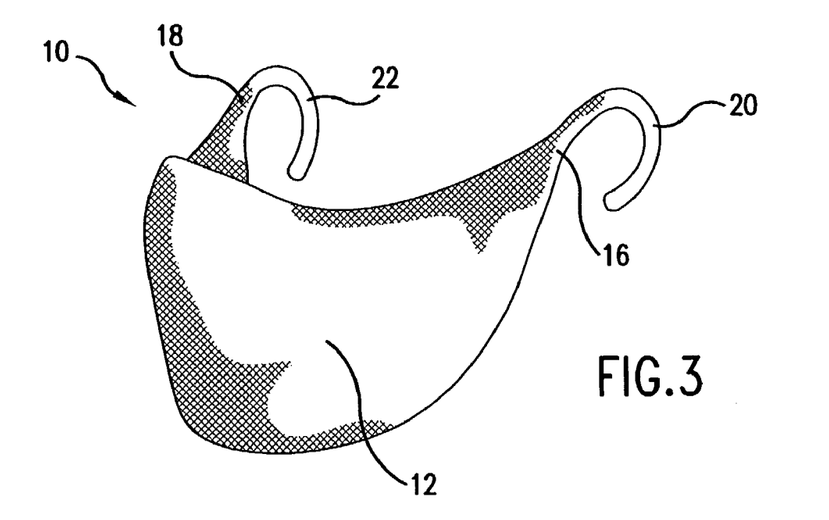
FIG. 3 is a perspective view of an exemplary embodiment of a face mask in accordance with the present invention.
Figure 4:
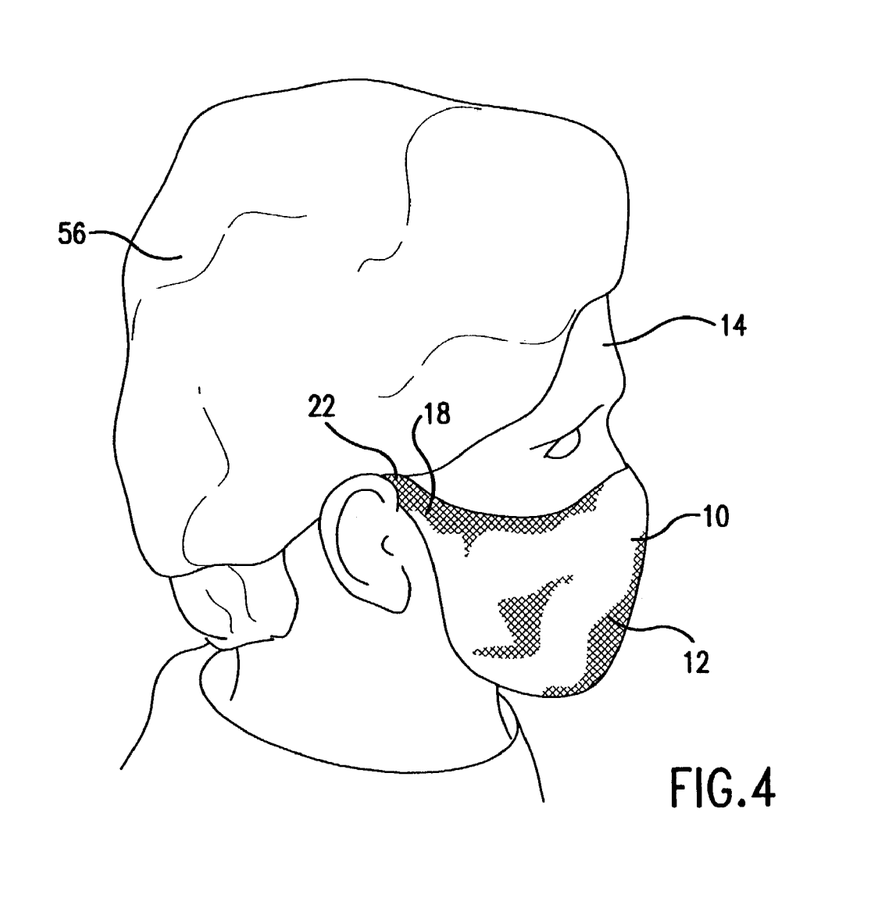
FIG. 4 is a perspective view of the exemplary embodiment of the face mask of FIG. 3 shown being worn by a user.

FIG. 3 shows an alternative exemplary embodiment of the face mask 10 of the present invention. Here, the left ear attachment member 20 forms a hook on the first extension portion 16. Additionally, the right ear attachment member 22 forms a hook on the second extension portion 18. FIG. 4 shows the face mask 10 of FIG. 3 being worn by the user 14. The second extension portion 18 wraps around the right ear of the user 14. Although, not shown, the left ear attachment member 20 wraps around the left ear of the user 14. In this manner, the face mask 10 is held onto the face of the user 14.

In other exemplary embodiments of the present invention, other ways of attaching the face mask 10 to the face of user 14 are possible. For instance, the right ear attachment member 22 may be provided with the aperture 26 as disclosed in FIG. 2 while the left ear attachment member 20 is provided with the hook section as shown in FIG. 3. Alternatively, the left ear attachment member 20 may be provided with the aperture 24 as disclosed in FIG. 1 while the right ear attachment member 22 is provided with the hook section as shown in FIG. 3. Additionally, the first extension portion 16 and the second extension portion 18 may be held onto the face of the user 14 through other methods. For instance, as shown in FIG. 4, a hair mask 56 is worn by the user 14 in order to prevent contamination from the hair of the user 14 from entering the environment. The hair mask 56 may be provided with an attachment member that connects the first and second extension portions 16 and 18 of the face mask 10 thereto. As such, the face mask 10 of the present invention is not limited to the attachment mechanisms shown in the drawings, but may be provided with various attachment mechanisms as is commonly known in the art.

Figure 5:
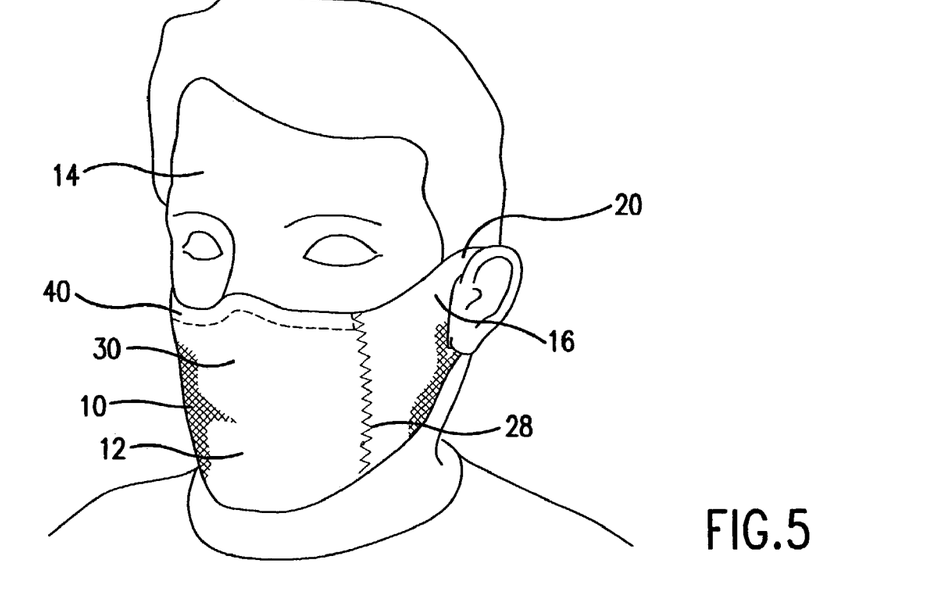
FIG. 5 is a perspective view of an exemplary embodiment of a face mask in accordance with the present invention being worn by a user. The face mask is shown as having a nose wire and at least one heat seal.

Although in its simplest form the face mask 10 is a single piece of material, in other exemplary embodiments of the present invention, the face mask 10 may be provided with one or more features. For instance, FIG. 5 shows the face mask 10 having at least one heat seal 28 imparted thereon. The heat seal 28 allows for a certain degree of structure to be imparted onto the body portion 12. For instance, the heat seal 28 may be placed in the body portion 12 so that a cavity 30 is formed therein. The cavity 30 may be formed by any process, heat sealing being only one way in which to form the cavity 30. The cavity 30 may be shaped so as to have the body portion 12 conform to the shape of the user's 14 face. In essence, the cavity 30 may be thought of as being a cup-like indentation in the body portion 12 into which the chin, mouth, and part of the nose of the user 14 may be placed. The cavity 30 may therefore allow for a better fit and improved sealing properties of the face mask 10.

Additionally, the face mask 10 of the present invention may be made of an elastic material that allows the face mask 10 to stretch in one or more directions. The use of an elastic material incorporated into the body portion 12, the first extension portion 16, and/or the second extension portion 18 may allow for fuller coverage of the user's 14 face and provide for more flexibility in accommodating variously sized faces of the users 14. Alternatively, the body portion 12, the first extension portion 16, and/or the second extension portion 18 may be made of an inelastic material. As such, the material that composes the face mask 10 may exhibit elastic characteristics depending upon the user's 14 needs.

Additionally, the face mask 10 may be provided with a nose wire 40 carried by the body portion 12. The use of the nose wire 40 is well known in the art. The nose wire 40 may be placed on the outside, inside, or within the body portion 12. The nose wire 40 may be a single piece of malleable metal that can be shaped by the user 14 or by the manufacturer in order to provide for an advantageous structure of the body portion 12. For instance, the nose wire 40 may be shaped so as to provide for a better fit of the body portion 12 proximate the nose and/or cheeks of the user 14. Such a better fit may help to prevent the transfer of pathogens through any possible openings that may exist along the upper periphery of the body portion 12. Although described as being a wire, any rigid material may be used in other exemplary embodiments.

Figure 6:
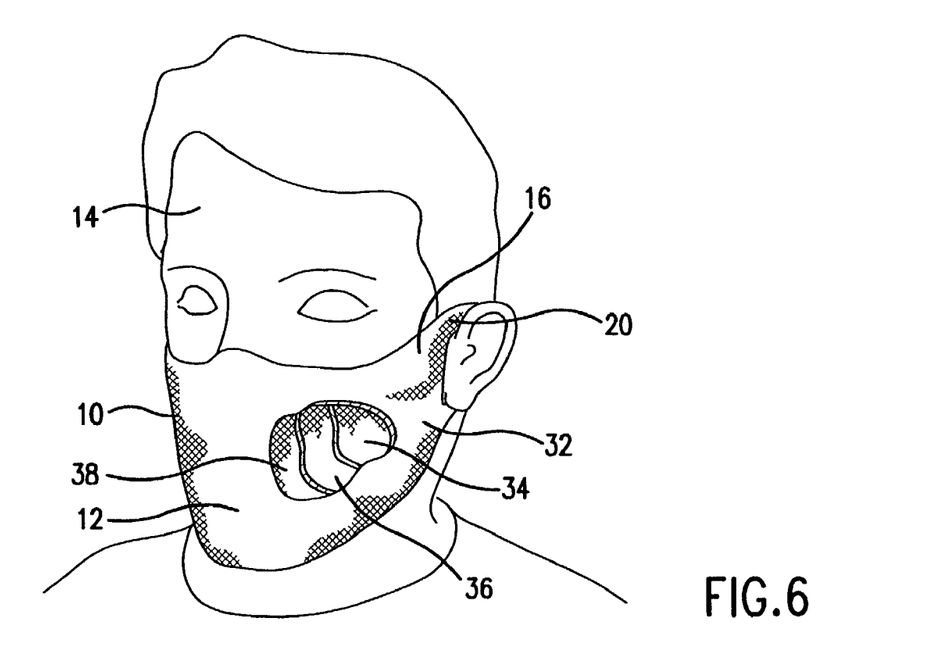
FIG. 6 is a perspective view of an exemplary embodiment of a face mask in accordance with the present invention being worn by a user. The face mask is shown as being multi-layered.

The face mask 10 of the present invention may also be composed of several layers as opposed to being a single piece of one layered material. FIG. 6 shows such a configuration where the face mask 10 is composed of four layers. Here, the body portion 12 is composed of a first layer 32, a second layer 34, a third layer 36, and a fourth layer 38. Although shown as having four layers, it is to be understood that in other exemplary embodiments of the present invention, that the body portion 12 and/or the entire face mask 10 may be made of any number of layers. In the exemplary embodiment shown in FIG. 6, the second layer 34 and the third layer 36 may be filter layers, and the first layer 32 and the fourth layer 38 may be outer and inner layers respectively that hold and contain the two filter layers 34 and 36. The layers 32, 34, 36, and 38 may be composed of the same material or may be made of different types of material. For instance SMS may be used to comprise the layers. SMS is a meltblown layer being made of meltblown fibers between two spunbond layers being made of spundbonded fibers. In addition, any material as described herein may be used along with those materials commonly known in the art. One of the layers 32, 34, 36, and 38 may provide for a barrier to the transmission of pathogenetic microorganism to and from the user 14. One or several of the layers of the face mask 10 may be a composite.

Figure 7:
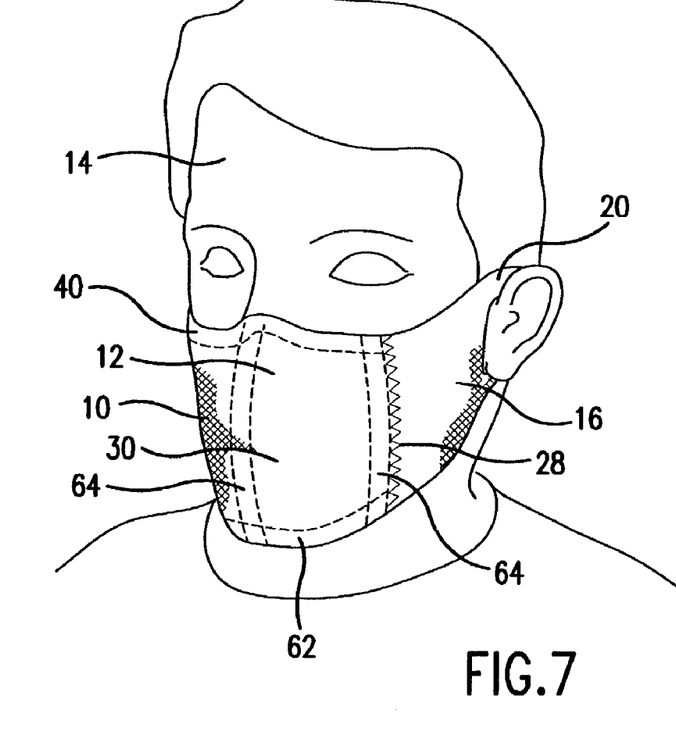

A further variation of the body portion 12 is disclosed in FIG. 7. Here, the body portion 12 carries the nose wire 40 on one end thereof, and a chin wire 62 on an opposite end thereof. The chin wire 62 may be a single piece of malleable metal that may be on the outside, inside, or within the body portion 12. The chin wire 62 may be formed so as to provided structure to the body portion 12 so that the body portion 12 tightly conforms against the chin of the user 14. The functionality of the chin wire 62 is therefore essentially the same as discussed above with respect to the nose wire 40.

Additionally, one or more body portion wires 64 may be carried by the body portion 12 at essentially right angles to the chin wire 62 and the nose wire 40. The body portion wires 64 may also be formed on the inside, outside, or within the body portion 12. The body portion wires 64 help to shape the body portion 12 so that the cavity 30 is formed therein. The cavity 30 may be shaped so that the body portion 12 contacts only the nose and chin of the user 14. Alternatively, the cavity 30 may be shaped so that the body portion 12 contacts a significant amount of the skin of the user's 14 face. For instance, the cavity 30 may be shaped so that the body portion 12 contacts the nose, cheeks, lips, and chin of the user 14. As such, the face mask 10 of the present invention is not limited to a body portion 12 that contacts or does not contact certain portions of the user's 14 face.

The cavity 30 may therefore be formed by the heat seal 28 and/or the use of wires 62, 64, and/or 40. The cavity 30 may allow for more movement of the jaw of the user 14 and may minimize the surface area of the body portion 12 that contacts the face of the user 14.

Figure 8:
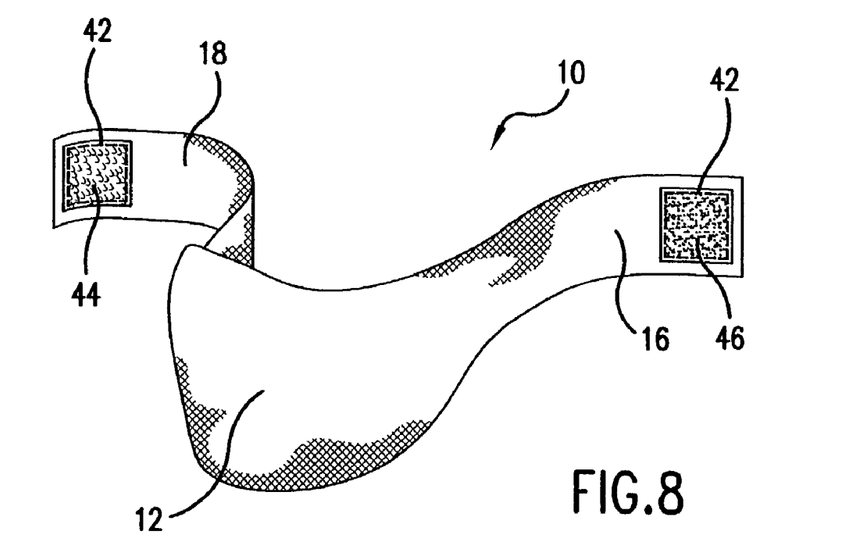
FIG. 8 is a perspective view of an exemplary embodiment of a face mask in accordance with the present. A hook and loop type fastener is present and is attached to a first and second extension portion of the face mask.

The face mask 10 of the present invention may also be configured so that the face mask 10 is retained on the user 14 through a mechanism other than contact of the ears of the user 14. For instance, as shown in FIG. 8, the face mask 10 may be provided with a hook and loop type fastener 42 that is carried on the first extension portion 16 and the second extension portion 18. In this exemplary embodiment, a loop section 46 is formed separately and attached to the first extension portion 16. Also, a hook section 44 is separately formed and attached to the second extension portion 18 of the face mask 10. The first and second extension portions 16 and 18 may be wrapped around the head of the user 14 and the hook and loop type fastener 42 engaged such that the first extension portion 16, second extension portion 18, and the body portion 12 are retained on the user 14. To disengage the hook and loop type fastener 42, the hook section 44 and the loop section 46 are to be pulled from one another. Although shown as being of equal size in FIG. 8, it is to be understood that in other exemplary embodiments of the present invention that the hook section 44 and the loop section 46 may be of different sizes. For instance, loop section 46 may be sized so as to extend along the entire length of the first extension portion 16. In this instance, the face mask 10 may be adjustable in order to fit on the face of users 14 of different sizes.

Figure 9:
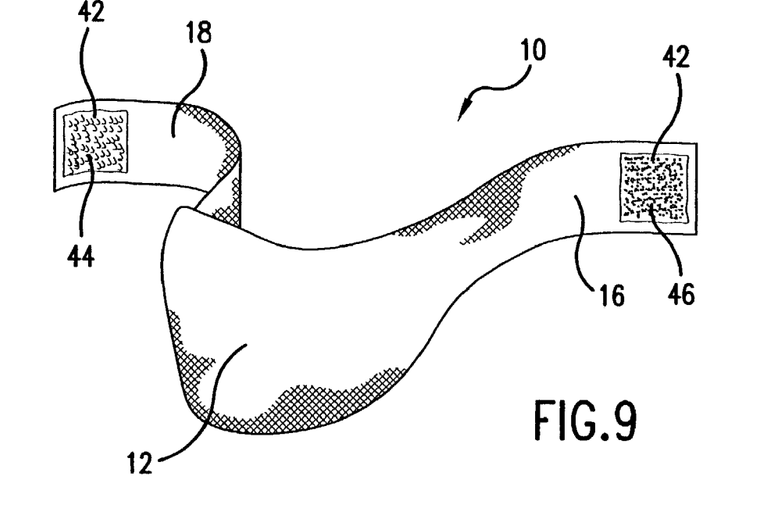
FIG. 9 is a perspective view of an exemplary embodiment of a face mask in accordance with the present invention. A hook and loop type fastener is present and is integrally formed on the first and second extension portions of the face mask.

FIG. 9 shows an alternative exemplary embodiment of the face mask 10 that employs the hook and loop type fastener 42. Here, the loop section 46 is integrally formed with the first extension portion 16, and is not a separate piece as disclosed in FIG. 8. Additionally, the hook section 44 is also an integrally formed component of the second extension portion 18 and is not a separate piece. However, in other exemplary embodiments of the present invention, the hook section 44 may be a separate piece while the loop section 46 is integrally formed with the first extension portion 16. Also, in still another exemplary embodiment of the present invention, the loop section 46 may be a separate component that is attached to the first extension portion 16 while the hook section 44 is integrally formed with second extension portion 18.

Figure 10:
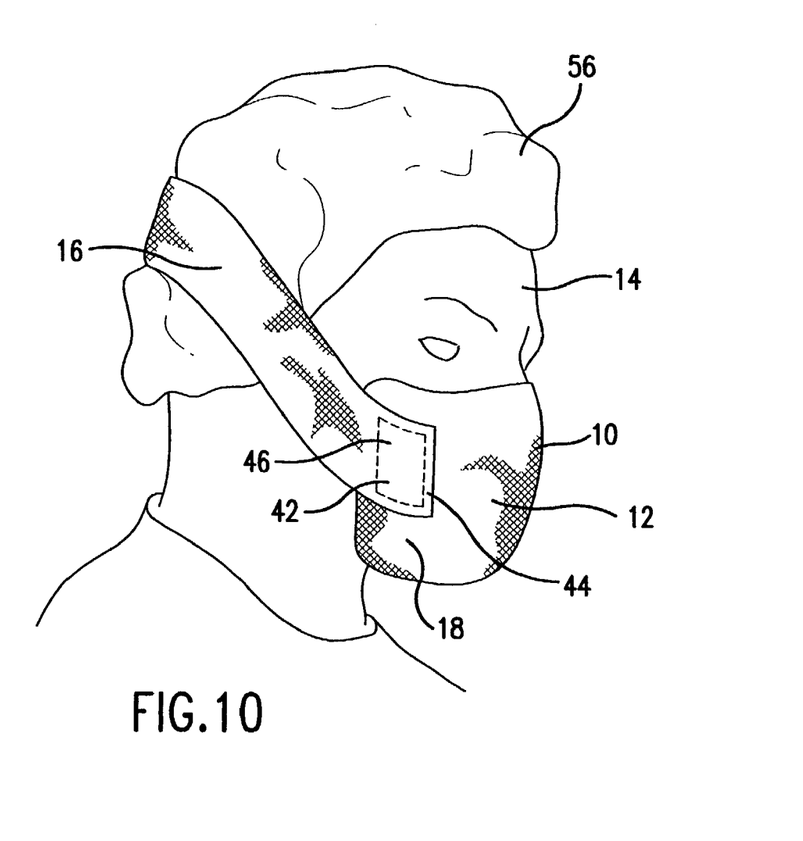
FIG. 10 is a perspective view of an exemplary embodiment of a face mask in accordance with the present invention. The face mask is shown being worn by a user, and the second extension portion of the face mask does not extend around the head of the user.

FIG. 10 shows an exemplary embodiment of the face mask 10 in accordance with the present invention where the second extension portion 18 does not extend around the head of the user 14. As such, the second extension portion 18 is integrally formed with the body portion 12 and is located proximate to the cheek of the user 14. By contrast, the first extension portion 16 extends around the head of the user 14. The first extension portion 16 is integrally formed with the body portion 12. The face mask 10 is again provided with the hook and loop type fastener 42 in order to engage the first extension portion 16 with the second extension portion 18 and to consequently retain the face mask 10 on the user 14. Disengagement of this exemplary embodiment is advantageous in that the user 14 need not reach around his or her head, but may simply detach the first extension portion 16 from the second extension portion 18 by reaching to his or her cheek.

Figure 11:
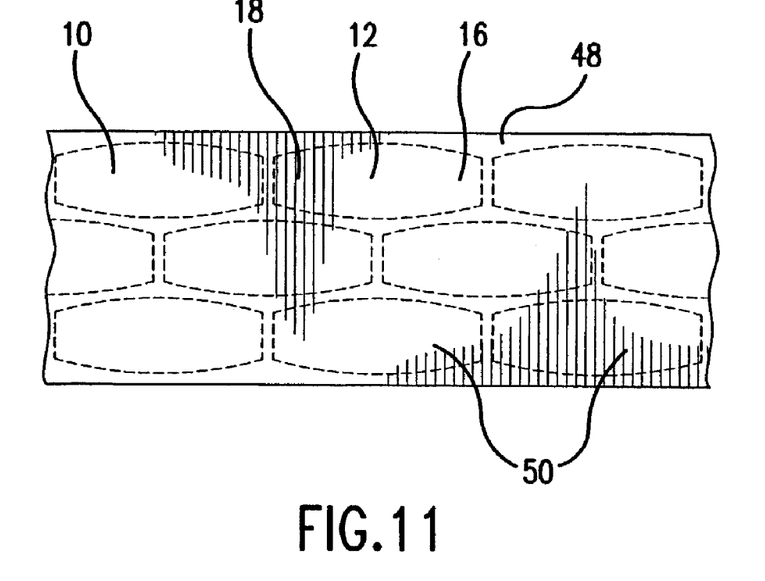
FIG. 11 is a plan view of a continuous web of material that has a plurality of face masks disposed therein.

The face mask 10 of the present invention may be formed on a continuous web of material 48 as shown in FIG. 11. Here, a plurality of face masks 50 are die cut into the continuous web of material 48. By having the face mask 10 be a single piece of material, it is therefore possible to quickly mass produce a large plurality of face masks 50 from a single continuous web of material 48. This type of manufacturing is advantageous in that several manufacturing steps are reduced or eliminated due to the fact that the face mask 10 is a single integral unit. As can be seen, the first extension portion 16, second extension portion 18, and the body portion 12 are all integrally formed with one another and are die cut from the continuous web of material 48 in one piece. The continuous web of material 48 may be of any size, and the plurality of face masks 50 may be cut therefrom in any number or shape.

Although described as being formed by die cutting, the plurality of face masks 50 may be formed in the continuous web of material 48 by other manufacturing processes known to those skilled in the art. For instance, any type of stamping process may be used to form the plurality of face masks 50. The stamping process may be, for instance three steps in which a plurality of body portions 12 are stamped, then a plurality of left or first extension portions 16 are stamped, and then a plurality of right or second extension portions 18 are stamped. However, the present invention is not limited to a three step manufacturing process.

Figure 12:
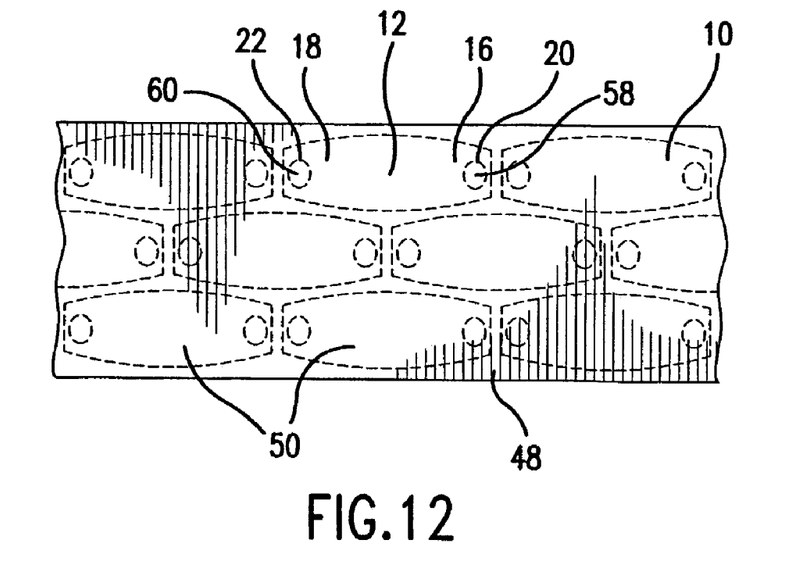
FIG. 12 is a plan view of a continuous web of material that has a plurality of face masks disposed therein. The face masks each contain a left and right punch out member.

FIG. 12 shows the plurality of face masks 50 being provided with a left punch out member 58 in the first extension portion 16, and a right punch out member 60 in the second extension portion 18. The left punch out member 58 may be removed from the first extension portion 16 so that the aperture 24 shown in FIG. 1 is formed therein. Additionally, the right punch out member 60 may be removed from the second extension portion 18 so that the aperture 26 shown in FIG. 1 is present. This process may be done after the user 14 has obtained the face mask 10, or may be done at a later stage of manufacturing prior to eventual purchase and use by the user 14. Additionally, the exemplary embodiment of the continuous web of material 48 shown in FIG. 12 may be modified so that apertures 24 and 26 as shown in FIG. 1 are formed in the first extension portion 16 and second extension portion 18 respectfully.

Figure 13A:
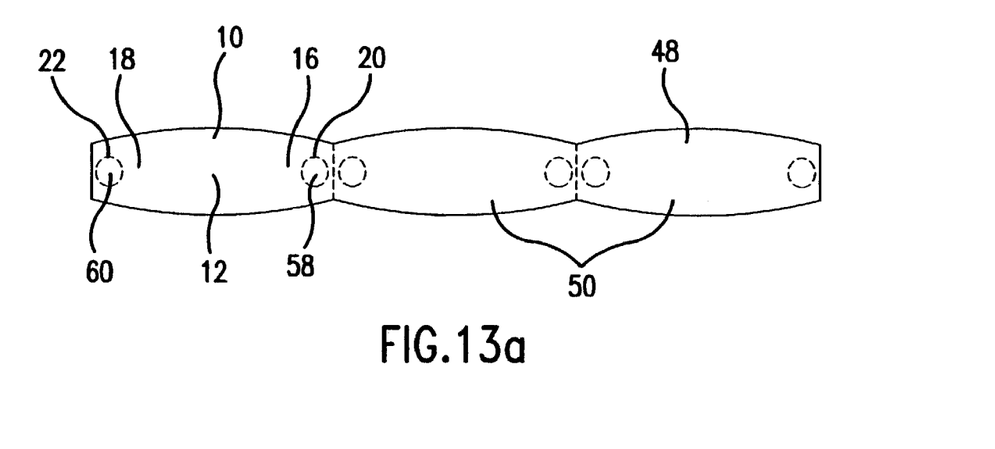
FIG. 13a is a plan view of a continuous web of material being a plurality of face masks.

FIG. 13a shows an alternative exemplary embodiment of the present invention where the continuous web of material 48 includes a series of the plurality of face masks 50 being connected to one another. The connection of the plurality of face masks 50 may, in one exemplary embodiment, be a perforated connection allowing for a user 14 to tear one of the plurality of face masks 50 from the other. It is to be understood that the present invention is not limited to a particular configuration, size or shape of the continuous web of material 48, but includes various configurations known in the art. The configuration shown in FIG. 13a is shown as an example.

Figure 13B:
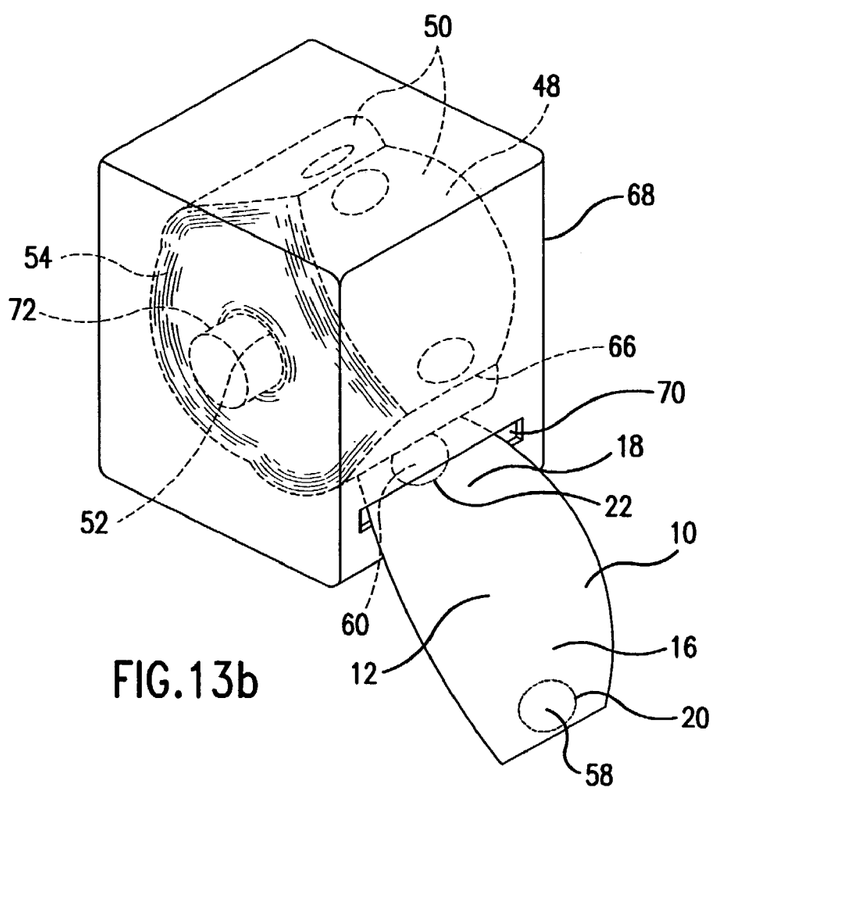
FIG. 13b is a perspective view of a roll of face masks formed by winding the continuous web of material shown in FIG. 13a around a cylindrical core and located within a housing.

FIG. 13b shows the continuous web of material 48 of FIG. 13a being rolled into a roll of face masks 54. Here, the continuous web of material 48 is rolled around a cylindrical core 52. This type of an arrangement allows for an advantageous dispensing configuration of the face mask 10. The user 14 may grasp the face mask 10 and pull the leading face mask 10 from the roll of face masks 54. The user may then detach the leading face mask 10 from the trailing face mask 10 by tearing a perforation between the two. A perforation 66 may be seen connecting two face masks 10 on the roll of face masks 54. However, in other exemplary embodiments, perforations 66 do not need to be present to remove the face masks 10 from one another. Additionally, other dispensing arrangements may be provided. For instance, the roll of face masks 54 may be provided with a mechanism that automatically detaches the leading face mask 10 from the trailing face mask 10. As such, the present invention provides for dispensing of the roll of face mask 54 in arrangements other than those disclosed in the drawings. The use of a single piece face mask 10 may allow for easier dispensing of the roll of face masks 54.

FIG. 13b shows the roll of face masks 54 being located within a housing 68 from which the face masks 10 are dispensed through a dispensing slot 70. The cylindrical core 52 is rotatably mounted on a member 72, although in other exemplary embodiments other ways of mounting the roll of face masks 54 may be used. The housing 68 acts to protect the roll of face masks 54 from the environment and provides for a convenient dispensing of face masks 10. Of course, various modifications to the housing 68 may be made in other exemplary embodiments of the present invention, and the invention is not limited to one particular style or configuration of the housing 68.

Figure 14A:
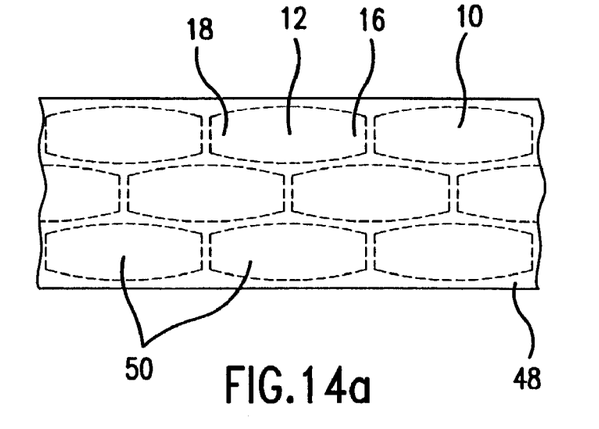
FIG. 14a is a plan view of a continuous web of material having a plurality of face masks disposed therein.
Figure 14B:
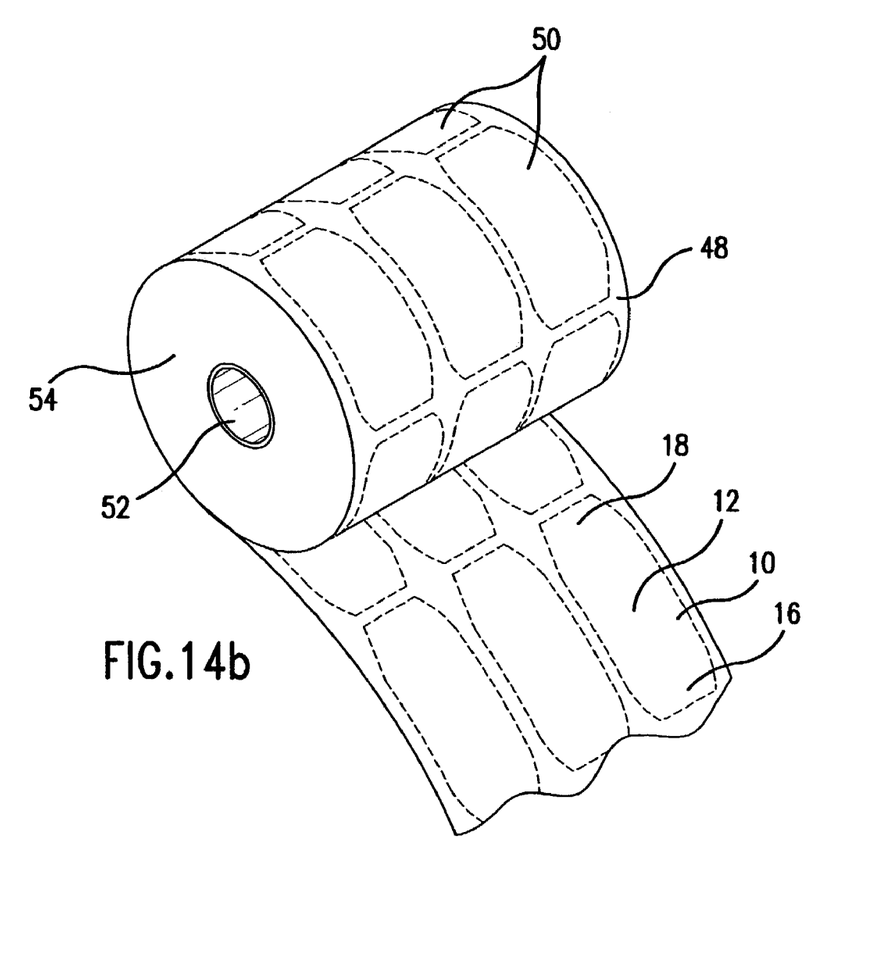
FIG. 14b is a perspective view of a roll of face masks formed by the continuous web of material shown in FIG. 14a by winding the web around a cylindrical core.

Additionally, FIG. 14a shows an alternative exemplary embodiment of the continuous web of material 48. The plurality of face masks 50 are disposed therein, and are wound onto a roll of face masks 54 as disclosed in FIG. 14b. Here, a series of face masks 10 are shown in alignment. The face masks 10 may be removed from the continuous web of material 48 by the user 14, or the embodiment shown in FIG. 14b may be transported to a separate manufacturing facility or area of the same manufacturing facility that further processes or adds features to the plurality of face masks 50 disposed within the continuous web of material 48.

The present invention relates to any style or configuration of the face mask 10 having integrally formed extension portions 16 and 18. The body portion 12 of the face mask 10 may be configured so that it is capable of stretching across the face of the user 14 from ear to ear and/or nose to chin. The ability of the body portion 12 to stretch and recover may provide the face mask 10 with better sealing capabilities and a more comfortable fit than face masks 10 that have an inelastic body portion 12. In order for the body portion 12 to stretch and recover, the body portion 12 must have at least one layer or a material that has stretch and recovery properties. Additionally, the entire face mask 10 may be composed of a material that has stretch and recovery properties in other exemplary embodiments of the present invention. In certain exemplary embodiments, the percent recovery is about 15% and the percent stretch is between 15–65%, in other embodiments the percent recovery is between 20–40% stretch, and in still other embodiments the percent recovery is about 25–30% stretch.

As mentioned, it should be appreciated that the present invention is not limited to any particular type or style of face mask 10, and that the styles shown in the Figs. are for illustrative purposes only. The integrally formed extension portions 16 and 18 disclosed in the present invention may be incorporated into any face mask 10 style or configuration, including rectangular masks, pleated masks, duck bill masks, cone masks, trapezoidal masks, etc. The face mask 10 according to the present invention may also incorporate any combination of known face mask 10 features, such as visors or shields, beard covers, etc. Exemplary faces masks are described and shown, for example, in the following U.S. Pat. Nos. 4,802,473; 4,969,457; 5,322,061; 5,383,450; 5,553,608; 5,020,533; and 5,813,398. These patents are incorporated herein in their entirety by reference for all purposes.

As stated, the face mask 10 may be composed of layers. These layers may be constructed from various materials known to those skilled in the art. For instance, the inner layer of the body portion 20 may be any nonwoven web, such as a spunbonded, meltblown, or coform nonwoven web or a bonded carded web. The inner layer of the body portion 20 and outer layer 50 may be a necked nonwoven web, a neck bonded laminate, or a reversibly necked nonwoven web. The inner layer of the body portion 20 and the outer layer 50 may be made of the same materials or different materials.

Many polyolefins are available for nonwoven web production, for example polyethylenes such as Dow Chemical's ASPUN® 6811A linear polyethylene, 2553 LLDPE and 25355, and 12350 polyethylene are such suitable polymers. Fiber forming polypropylenes include, for example, Exxon Chemical Company's Escorene® PD 3445 polypropylene and Himont Chemical Co.'s PF-304. Many other suitable polyolefins are commercially available.

If an elastic first extension portion 16, second extension portion 18, or body portion 12 is desired, the elastic properties may be imparted from the degree of elasticity of the first extension portion 16, second extension portion-18, and/or or body portion 12. The material used may be a necked nonwoven web, a reversibly necked nonwoven material, and elastic materials such as an elastic coform material, an elastic meltblown nonwoven web, a plurality of elastic filaments, an elastic film, or a combination thereof. Such elastic materials have been incorporated into composites, for example, in U.S. Pat. No. 5,681,645 to Strack et al., U.S. Pat. No. 5,493,753 to Levy et al., U.S. Pat. No. 4,100,324 to Anderson et al., and in U.S. Pat. No. 5,540,976 to Shawver et al, the contents of which are incorporated herein by reference in their entirety for all purposes. In an exemplary embodiment where an elastic film is used on the body portion 12, the film must be sufficiently perforated to ensure that the user 14 can breathe through the body portion 12.

Elastomeric thermoplastic polymers may be used in the face mask 10 of the present invention and may include block copolymers having the general formula A-B-A' or A-B, where A and A' are each a thermoplastic polymer endblock which contains a styrenic moiety such as a poly (vinyl arene) and where B is an elastomeric polymer midblock such as a conjugated diene or a lower alkene polymer. Block copolymers of the A-B-A' type can have different or the same thermoplastic block polymers for the A and A' blocks, and the present block copolymers are intended to embrace linear, branched and radial block copolymers. Examples of useful elastomeric resins include those made from block copolymers such as polyurethanes, copolyether esters, polyamide polyether block copolymers, ethylene vinyl acetates (EVA), block copolymers having the general formula A-B-A' or A-B like copoly(styrene/ethylene-butylene), styrene-poly(ethylene-propylene)-styrene, styrene-poly(ethylene-butylene)-styrene, (polystyrene/poly(ethylene-butylene)/polystyrene, poly(styrene/ethylene-butylene/styrene) and the like. The filter 32 may be made of a meltblown nonwoven web and, in some embodiments, may be an electret. Electret treatment results in a charge being applied to the filter which further increases filtration efficiency by drawing particles to be filtered toward the filter by virtue of their electrical charge.

Electret treatment can be carried out by a number of different techniques. One technique is described in U.S. Pat. No. 5,401,446 to Tsai et al. assigned to the University of Tennessee Research Corporation and incorporated herein by reference in its entirety for all purposes. Other methods of electret treatment are known in the art, such as that described in U.S. Pat. No. 4,215,682 to Kubik et al., U.S. Pat. No. 4,375,718 to Wadsworth, U.S. Pat. No. 4,592,815 to Nakao and U.S. Pat. No. 4,874,659 to Ando, the contents of which are incorporated herein by reference in their entirety.

A filter, for instance the body portion 12, may be made of an expanded polytetrafluoroethylene (PTFE) membrane, such as those manufactured by W. L. Gore & Associates. A more complete description of the construction and operation of such materials can be found in U.S. Pat. No. 3,953,566 to Gore and U.S. Pat. No. 4,187,390 to Gore, the contents of which are incorporated herein by reference in their entirety. The expanded polytetrafluoroethylene membrane may be incorporated into a multi-layer composite, including, but not limited to, an outer nonwoven web layer, an extensible and retractable layer, and an inner layer comprising a nonwoven web.

Multiple layers of the face mask 10 may be joined by various methods, including adhesive bonding, thermal bonding, or ultrasonic bonding. Additionally, the hook and loop type fastener 42 may be affixed to the face mask 10 by one or more of these previously mentioned methods of joining the layers of the face mask 10.

The body portion 12 of the face mask 10 and/or the first and/or second extension portions 16 and 18 may be made of a composite that is a neck bonded laminate in certain exemplary embodiments of the present invention. The neck bonded laminate may utilize a necked material or a reversibly necked material. The necking process typically involves unwinding a material from a supply roll and passing it through a brake nip roll assembly at a given linear-speed. A take-up roll or nip, operating at a linear speed greater than that of the brake nip roll, draws the material and generates the tension needed to elongate and neck the fabric. When a reversibly necked material is desired, the stretched material is heated and cooled while in a stretched condition. The heating and cooling of the stretched material causes additional crystallization of the polymer and imparts a heat set. The necked material or reversibly necked material is then bonded to an elastic material. The resulting necked composite is extensible and retractable in the cross-machine direction, that is the direction perpendicular to the direction the material is moving when it is produced. Upon extension and release, the elastic material provides the force needed for the extended composite to retract. A composite of multiple layers may also be formed in this fashion, either simultaneously or step-wise. As an illustration, to construct a four-layer composite, a layer of a spunbonded nonwoven, another layer of a spunbonded nonwoven, and a meltblown nonwoven material are individually necked by the process detailed above. The layers are then positioned as desired and thermally bonded to an elastomeric meltblown web. The resulting composite is extensible and retractable in at least one direction.

In another exemplary embodiment, the composite may be a stretch bonded laminate. A stretch bonded laminate is formed by providing an elastic material, such as a nonwoven web, filaments, or film, extending the elastic material, attaching it to a gatherable material, and releasing the resulting laminate. A stretch bonded laminate is extensible and retractable in the machine direction, that is the direction that the material is moving when it is produced. A composite with multiple layers may be formed by providing the elastic layer and the gatherable layers, and subjecting it to this process either simultaneously or stepwise. The stretch bonded laminate may also include a necked material that is extensible and retractable in the cross-direction such that the overall laminate is extensible and retractable in at least two dimensions. As an illustration, to construct a two-layer composite that is extensible and retractable in at least two dimensions, an elastomeric meltblown nonwoven web is provided, the elastomeric meltblown nonwoven web is then extended in the machine direction, and the necked spunbonded nonwoven material is attached to the elastomeric meltblown nonwoven web by thermal bonding while the elastomeric meltblown web is extended. When the biasing force is released, the resulting composite is extensible and retractable in both the cross-direction and machine direction, due to the extensibility of the necked material and the use of the stretch bonding process, respectively.

Additional examples of processes to make such composites are described in, but not limited to, U.S. Pat. No. 5,681,645 to Strack et al., U.S. Pat. No. 5,492,753 to Levy et al., U.S. Pat. No. 4,100,324 to Anderson et al., and in U.S. Pat. No. 5,540,976 to Shawver et al., the contents of which are incorporated herein by reference in their entirety for all purposes.

The composite may contain various chemical additives or topical chemical treatments in or on one or more layers, including, but not limited to, surfactants, colorants, antistatic chemicals, antifogging chemicals, fluorochemical blood or alcohol repellents, lubricants, or antimicrobial treatments.

It should be understood that the present invention includes various modifications that can be made to the exemplary embodiments of the face mask 10 described herein as come within the scope of the appended claims and their equivalents.

What is claimed is:

1. A dispenser assembly for dispensing face masks, comprising:
 a housing;
 a core carried by said housing; and
 a roll of face masks rotatably disposed on said core, at least one of said face masks comprising:
  a body portion that is multi-layered having at least two layers that include different materials;
  a left extension portion integrally attached to said body portion;
  a right extension portion integrally attached to said body portion; and
 wherein said roll of face masks is a continuous web of material having said face masks disposed therein.

2. The dispenser assembly of claim 1, wherein said roll of face masks has perforations between said right and left extension portions of said face masks so that said face masks are disengaged from one another by tearing said perforations between said face masks.

3. The dispenser assembly of claim 1, wherein said roll of face masks has a length and a width so that three of said face masks are disposed across the width of said roll of face masks.

4. The dispenser assembly of claim 1, wherein said left extension portion of each face mask comprises an aperture therethrough, and said right extension portion of each face mask comprises an aperture therethrough.

5. The dispenser assembly of claim 1, wherein each of said left and right extension portions comprise punch out members.

6. The dispenser assembly of claim 1, wherein said core is cylindrical in shape.

7. The dispenser assembly of claim 1, wherein said roll of face masks are dispensed from said core by pulling a leading face mask from said roll of face masks and disengaging said leading face mask from a trailing face mask.

8. The dispenser assembly of claim 1, wherein said roll of face masks are dispensed from said core by disengaging one of said face masks from said continuous web of material.

9. A roll of face masks, comprising a continuous web of material having a plurality of face masks disposed therein, at least one of said plurality of face masks has a body portion and a left extension portion integrally attached to said body portion and a right extension portion integrally attached to said body portion, wherein said body portion is multi-layered and has at least two layers that include different materials.

10. The roll of face masks as set forth in claim 9, wherein each face mask body portion comprises said left extension portion and said right extension portion integrally attached to said body portion.

11. The roll of face masks as set forth in claim 9, comprising a plurality of perforations disposed between said face masks for disengaging said face masks from one another by tearing said perforations between said face masks.

12. The roll of face masks as set forth in claim 9, wherein said continuous web of material has a length and a width, and wherein three different face masks of said plurality of face masks are located across the width of said roll of face masks.

13. The roll of face masks as set forth in claim 9, wherein each of said left and right extension portions comprise an aperture.

14. The roll of face masks as set forth in claim 9, wherein each of said left and right extension portions comprise punch out members.

15. The roll of face masks as set forth in claim 9, wherein said continuous web of material is rolled into a substantially cylindrical shape having a substantially cylindrical cavity extending there-through.

16. The roll of face masks as set forth in claim 9, wherein said continuous web of material comprises material located between said plurality of face masks.

17. The roll of face masks as set forth in claim 12, wherein said plurality of face masks are located in three rows across said width of said continuous web, and wherein all of said plurality of face masks are evenly spaced along said length of said continuous web.

18. The roll of face masks as set forth in claim 12, wherein said plurality of face masks are located in three rows across said width of said continuous web, and wherein at least one of said rows is staggered along the length of said continuous web with respect to the other of said rows.

* * * * *